(12) United States Patent
Hamada et al.

(10) Patent No.: US 8,835,022 B2
(45) Date of Patent: Sep. 16, 2014

(54) METAL COMPLEX COMPOUND AND ORGANIC LIGHT EMITTING DIODE DEVICE INCLUDING THE SAME

(75) Inventors: Yuji Hamada, Yongin (KR); Kwan-Hee Lee, Yongin (KR)

(73) Assignee: Samsung Display Co., Ltd., Yongin (KR)

( * ) Notice: Subject to any disclaimer, the term of this patent is extended or adjusted under 35 U.S.C. 154(b) by 335 days.

(21) Appl. No.: 13/181,449

(22) Filed: Jul. 12, 2011

(65) Prior Publication Data

US 2012/0074389 A1 Mar. 29, 2012

(30) Foreign Application Priority Data

Sep. 27, 2010 (KR) ................... 10-2010-0093351

(51) Int. Cl.
| | | |
|---|---|---|
| H01L 51/54 | (2006.01) | |
| C09K 11/06 | (2006.01) | |
| C07F 3/00 | (2006.01) | |
| C07D 215/30 | (2006.01) | |
| C07D 221/10 | (2006.01) | |
| H01L 51/00 | (2006.01) | |
| H01L 51/50 | (2006.01) | |

(52) U.S. Cl.
CPC .......... *H01L 51/0092* (2013.01); *C07D 215/30* (2013.01); *C07D 221/10* (2013.01); *H01L 51/0077* (2013.01); *H01L 51/5012* (2013.01); *H01L 51/0072* (2013.01); *H01L 51/0085* (2013.01); *H01L 51/006* (2013.01); *H01L 51/5048* (2013.01); *H01L 51/0061* (2013.01); *Y10S 428/917* (2013.01)
USPC .......... 428/690; 428/917; 313/504; 313/506; 257/40; 257/E51.024; 546/79

(58) Field of Classification Search
None
See application file for complete search history.

(56) References Cited

U.S. PATENT DOCUMENTS

| | | | |
|---|---|---|---|
| 5,858,563 A * | 1/1999 | Sano et al. ................... | 428/690 |
| 2002/0076576 A1* | 6/2002 | Li et al. ........................ | 428/690 |
| 2004/0247937 A1* | 12/2004 | Chen et al. ................... | 428/690 |

FOREIGN PATENT DOCUMENTS

| | | |
|---|---|---|
| JP | 05-214333 | 8/1993 |
| JP | 05-331460 | 12/1993 |
| JP | 3071091 B | 11/1994 |
| JP | 07-197021 | 8/1995 |
| JP | 2000-012222 | 1/2000 |
| WO | WO 2010075421 A2 * | 7/2010 .............. H01L 51/00 |

* cited by examiner

*Primary Examiner* — Andrew K Bohaty

(74) *Attorney, Agent, or Firm* — Knobbe Martens Olson & Bear LLP

(57) ABSTRACT

Disclosed are a metal complex compound represented by the following Chemical Formula 1 or 3, and an organic light emitting diode device including the same.

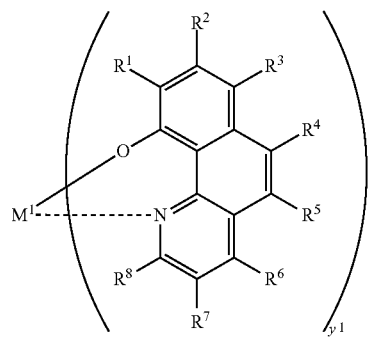

[Chemical Formula 1]

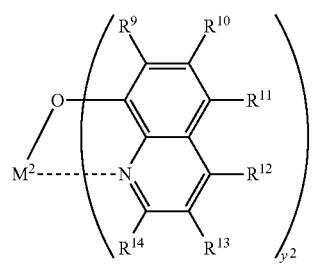

[Chemical Formula 3]

In Chemical Formulae 1 and 3, $M^1$, $M^2$, $R_1$ to $R_{14}$, $y_1$ and $y_2$ are as defined in the detailed description.

9 Claims, 1 Drawing Sheet

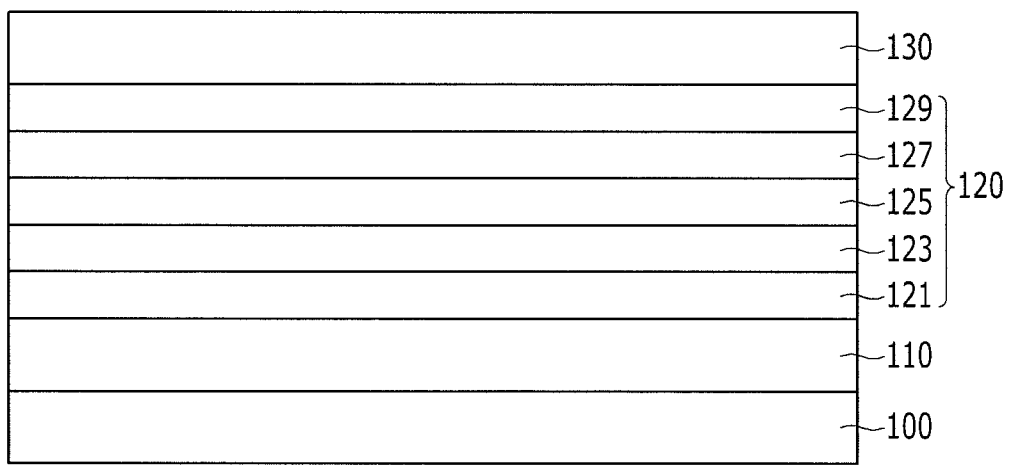

METAL COMPLEX COMPOUND AND ORGANIC LIGHT EMITTING DIODE DEVICE INCLUDING THE SAME

CROSS-REFERENCE TO RELATED APPLICATIONS

This application claims priority to and the benefit of Korean Patent Application No. 10-2010-0093351 filed in the Korean Intellectual Property Office on Sep. 27, 2010, the entire contents of which are incorporated herein by reference.

BACKGROUND

1. Field

This disclosure relates to a metal complex compound and an organic light emitting diode device including the same.

2. Description of the Related Technology

Organic light emitting diode (OLED) devices have been drawing attention as a display device and a luminous device. An organic light emitting diode device includes two electrodes and an emission layer interposed therebetween, and emits light when electrons injected from one electrode are combined with holes injected from another electrode in an emission layer to generate excitons that release energy. Since the organic light emitting diode device emits light in itself without a particular light source, it has excellent response speed, viewing angle, and contrast ratio as well as low power consumption. An organic light emitting diode device has been required to have increased luminous efficiency but decreased driving voltage.

SUMMARY

One aspect of this disclosure provides a metal complex compound being capable of increasing luminous efficiency and reducing a driving voltage.

Another aspect of this disclosure provides an organic light emitting diode device including the metal complex compound.

According to one aspect of this disclosure, provided is a metal complex compound represented by the following Chemical Formula 1.

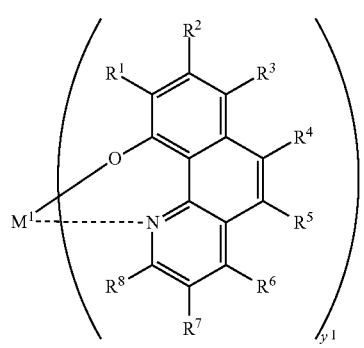

[Chemical Formula 1]

In Chemical Formula 1, $M^1$ is a Group 2 metal ion or Group 3 metal ion, $R^1$ to $R^8$ are the same or different, and are hydrogen, deuterium, a halogen, a hydroxyl group, a substituted or unsubstituted $C_1$ to $C_{20}$ alkyl group, a substituted or unsubstituted $C_2$ to $C_{20}$ alkenyl group, a substituted or unsubstituted $C_2$ to $C_{20}$ alkynyl group, a substituted or unsubstituted $C_1$ to $C_{20}$ alkoxy group, a substituted or unsubstituted $C_3$ to $C_{30}$ cycloalkyl group, a substituted or unsubstituted $C_3$ to $C_{30}$ cycloalkenyl group, a substituted or unsubstituted $C_3$ to $C_{30}$ cycloalkynyl group, a substituted or unsubstituted $C_2$ to $C_{30}$ heterocycloalkyl group, a substituted or unsubstituted C2 to C30 heterocycloalkenyl group, a substituted or unsubstituted $C_2$ to $C_{30}$ heterocycloalkynyl group, a substituted or unsubstituted $C_6$ to $C_{30}$ an aryl group, a substituted or unsubstituted $C_6$ to $C_{30}$ aryloxy group, a substituted or unsubstituted $C_2$ to $C_{30}$ heteroaryl group, an amine group, an ester group, a carboxyl group, a nitro group, or a cyano group, provided that at least one of $R^1$ to $R^8$ is deuterium, and $y^1$ is 2 or 3.

In Chemical Formula 1, $M^1$ may be Be, Zn, Mg, Al, Ga, In, or a combination thereof.

The metal complex compound may be represented by one of the following Chemical Formulae 2-1 to 2-10.

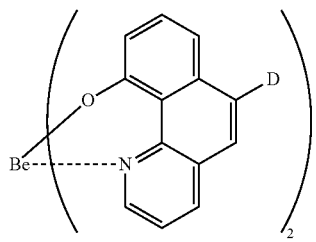

[Chemical Formula 2-1]

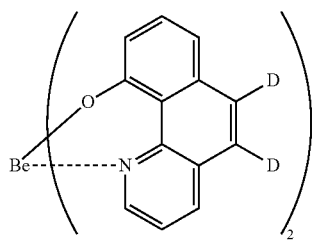

[Chemical Formula 2-2]

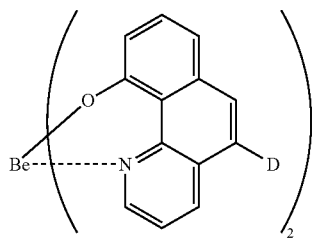

[Chemical Formula 2-3]

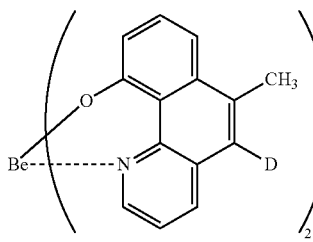

[Chemical Formula 2-4]

-continued

[Chemical Formula 2-5]

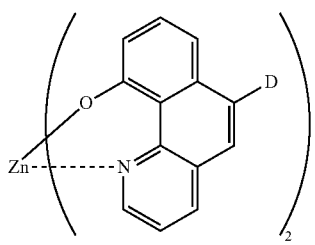

[Chemical Formula 2-6]

[Chemical Formula 2-7]

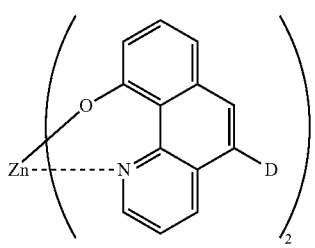

[Chemical Formula 2-8]

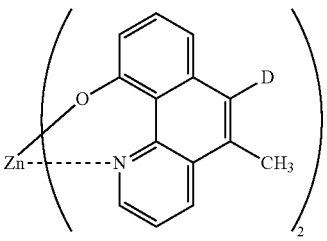

[Chemical Formula 2-9]

[Chemical Formula 2-10]

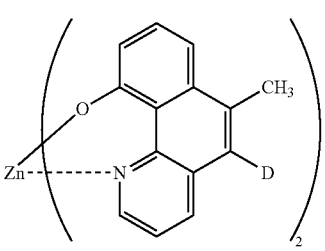

According to another aspect of this disclosure, a metal complex compound represented by the following Chemical Formula 3 is provided.

[Chemical Formula 3]

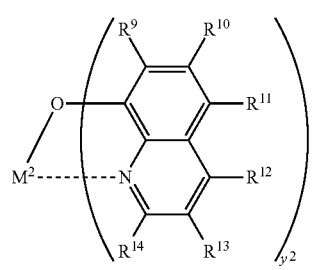

In Chemical Formula 3, $M^2$ is a Group 2 metal ion or Group 3 metal ion, $R^9$ to $R^{14}$ are the same or different, and are hydrogen, deuterium, a halogen, a hydroxyl group, a substituted or unsubstituted $C_1$ to $C_{20}$ alkyl group, a substituted or unsubstituted $C_2$ to $C_{20}$ alkenyl group, a substituted or unsubstituted $C_2$ to $C_{20}$ alkynyl group, a substituted or unsubstituted $C_1$ to $C_{20}$ alkoxy group, a substituted or unsubstituted $C_3$ to $C_{30}$ cycloalkyl group, a substituted or unsubstituted $C_3$ to $C_{30}$ cycloalkenyl group, a substituted or unsubstituted $C_3$ to $C_{30}$ cycloalkynyl group, a substituted or unsubstituted $C_2$ to $C_{30}$ heterocycloalkyl group, a substituted or unsubstituted $C_2$ to $C_{30}$ heterocycloalkenyl group, a substituted or unsubstituted $C_2$ to $C_{30}$ heterocycloalkynyl group, a substituted or unsubstituted $C_6$ to $C_{30}$ an aryl group, a substituted or unsubstituted $C_6$ to $C_{30}$ aryloxy group, a substituted or unsubstituted $C_2$ to $C_{30}$ heteroaryl group, an amine group, an ester group, a carboxyl group, a nitro group, or a cyano group, provided that at least one of $R^9$ to $R^{14}$ is deuterium, and $y^2$ is 2 or 3.

In Chemical Formula 3, $M^2$ may be Be, Zn, Mg, Al, Ga, In, or a combination thereof.

The metal complex compound may be represented by one of the following Chemical Formulae 4-1 to 4-10.

[Chemical Formula 4-1]

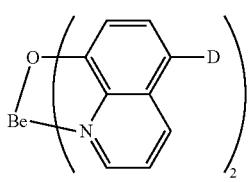

[Chemical Formula 4-2]

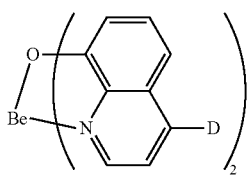

[Chemical Formula 4-3]

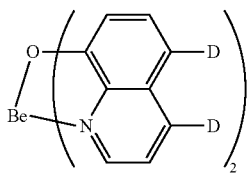

[Chemical Formula 4-4]

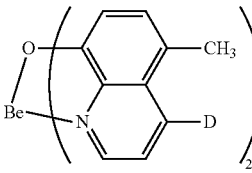

[Chemical Formula 4-5]

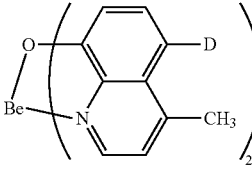

[Chemical Formula 4-6]

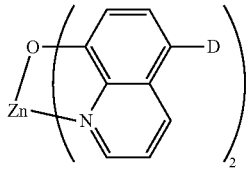

[Chemical Formula 4-7]

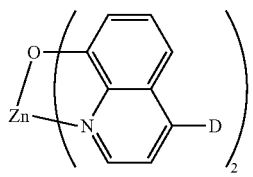

[Chemical Formula 4-8]

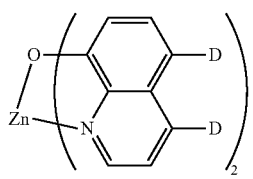

[Chemical Formula 4-9]

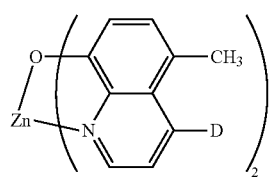

[Chemical Formula 4-10]

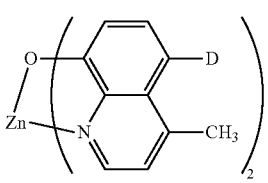

According to yet another aspect of this disclosure, an organic light emitting device is provided, which includes a first electrode, a second electrode facing the first electrode, and an organic layer interposed between the first electrode and the second electrode, wherein the organic layer includes a metal complex compound represented by the above Chemical Formula 1.

According to still another aspect of this disclosure, an organic light emitting device is provided, which includes a first electrode, a second electrode facing the first electrode, and an organic layer interposed between the first electrode and the second electrode, wherein the organic layer includes a metal complex compound represented by the above Chemical Formula 3.

The organic layer may include at least one among a hole injection layer, a hole transport layer, an emission layer, an electron transport layer, and an electron injection layer that are sequentially positioned on the first electrode. The metal complex compound may be included in the emission layer or the electron transport layer.

Further aspects of this disclosure are described in more detail.

Luminous efficiency of an organic light emitting device is improved, while reducing its driving voltage.

BRIEF DESCRIPTION OF THE DRAWINGS

FIG. 1 is the schematic cross-sectional view of an organic light emitting diode device according to one embodiment.

DETAILED DESCRIPTION

The present disclosure will be described more fully hereinafter with reference to the accompanying drawings, in which example embodiments of this disclosure are shown. This disclosure may, however, be embodied in many different forms and is not construed as limited to the example embodiments set forth herein.

In the drawings, the thickness of layers, films, panels, regions, etc., may be exaggerated for clarity. Like reference numerals designate like elements throughout the specification. It will be understood that when an element such as a layer, film, region, or substrate is referred to as being "on" another element, it can be directly on the other element or intervening elements may also be present. In contrast, when an element is referred to as being "directly on" another element, there are no intervening elements present.

As used herein, when a definition is not otherwise provided, the term "substituted" refers to one substituted with a halogen, a hydroxy group, a $C_1$ to $C_{20}$ alkyl group, a $C_2$ to $C_{20}$ alkenyl group, a $C_2$ to $C_{20}$ alkynyl group, a $C_1$ to $C_{20}$ alkoxy group, a $C_3$ to $C_{30}$ cycloalkyl group, a $C_3$ to $C_{30}$ cycloalkenyl group, a $C_3$ to $C_{30}$ cycloalkynyl group, a $C_2$ to $C_{30}$ heterocycloalkyl group, a $C_2$ to $C_{30}$ heterocycloalkenyl group, a $C_2$ to $C_{30}$ heterocycloalkynyl group, a $C_6$ to $C_{30}$ aryl group, a $C_6$ to $C_{30}$ aryloxy group, a $C_2$ to $C_{30}$ heteroaryl group, an amine group (—NR'R", wherein R' and R" are the same or different, and are hydrogen, a $C_1$ to $C_{20}$ alkyl group or a $C_6$ to $C_{30}$ aryl group), an ester group (—COOR'", wherein R'" is hydrogen, a $C_1$ to $C_{20}$ alkyl group or a $C_6$ to $C_{30}$ aryl group), a carboxyl group (—COOH), a nitro group (—NO$_2$) or a cyano group (—CN).

As used herein, when a definition is not otherwise provided, the terms "heterocycloalkyl group", "heterocycloalkenyl group", "heterocycloalkynyl group" and "heteroaryl group" respectively refer to a cycloalkyl group, a cycloalkenyl group, a cycloalkynyl group, and an aryl group including at least one of N, O, S, and P in their rings.

The metal complex compound according to one embodiment may be represented by the following Chemical Formula 1.

[Chemical Formula 1]

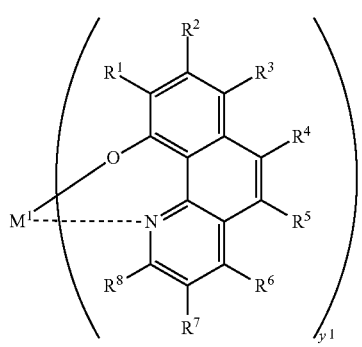

In Chemical Formula 1,
$M^1$ is a Group 2 metal ion or Group 3 metal ion,
$R^1$ to $R^8$ are the same or different, and are hydrogen, deuterium (D), a halogen, a hydroxyl group, a substituted or unsubstituted $C_1$ to $C_{20}$ alkyl group, a substituted or unsubstituted $C_2$ to $C_{20}$ alkenyl group, a substituted or unsubstituted $C_2$ to $C_{20}$ alkynyl group, a substituted or unsubstituted $C_1$ to $C_{20}$ alkoxy group, a substituted or unsubstituted $C_3$ to $C_{30}$ cycloalkyl group, a substituted or unsubstituted $C_3$ to $C_{30}$ cycloalkenyl group, a substituted or unsubstituted $C_3$ to $C_{30}$ cycloalkynyl group, a substituted or unsubstituted $C_2$ to $C_{30}$ heterocycloalkyl group, a substituted or unsubstituted $C_2$ to $C_{30}$ heterocycloalkenyl group, a substituted or unsubstituted $C_2$ to $C_{30}$ heterocycloalkynyl group, a substituted or unsubstituted $C_6$ to $C_{30}$ an aryl group, a substituted or unsubstituted $C_6$ to $C_{30}$ aryloxy group, a substituted or unsubstituted $C_2$ to $C_{30}$ heteroaryl group, an amine group, an ester group, a carboxyl group, a nitro group, or a cyano group, provided that at least one of $R^1$ to $R^8$ is deuterium, and $y^1$ is 2 or 3.

$R^1$ to $R^8$ are ligands of the metal a complex compound. When the ligands comprise at least one deuterium, it can bind with carbon more strongly than light isotope hydrogen, and therefore the metal complex compound having deuterium show a decreased substituted reaction activity. From this result, chemical stability of the metal complex compound is improved and thus the metal complex compound may be usefully applicable as an organic material of an organic light emitting diode device.

In Chemical Formula 1, $M^1$ may be Be, Zn, Mg, Al, Ga, In, or a combination thereof.

Examples of the metal complex compound may include one of the following Chemical Formulae 2-1 to 2-10, but are not limited thereto.

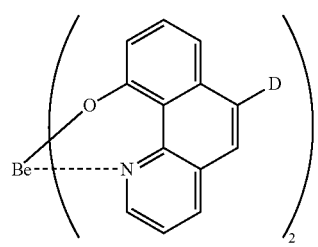

[Chemical Formula 2-1]

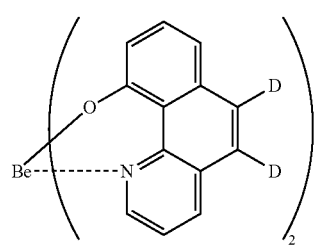

[Chemical Formula 2-2]

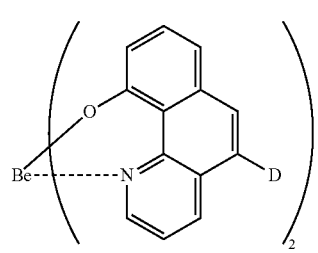

[Chemical Formula 2-3]

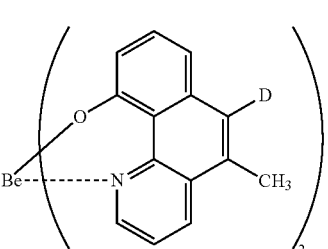

[Chemical Formula 2-4]

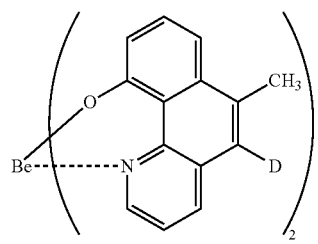

[Chemical Formula 2-5]

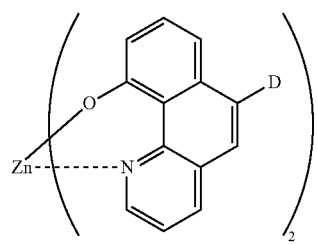

[Chemical Formula 2-6]

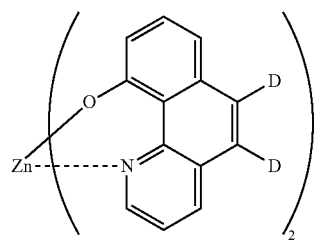

[Chemical Formula 2-7]

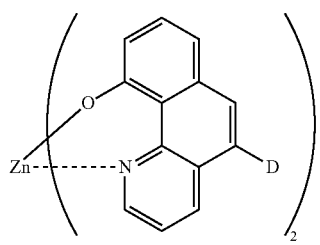

[Chemical Formula 2-8]

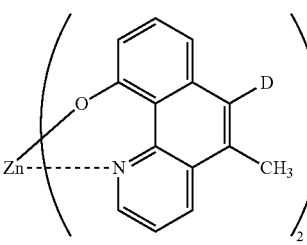

[Chemical Formula 2-9]

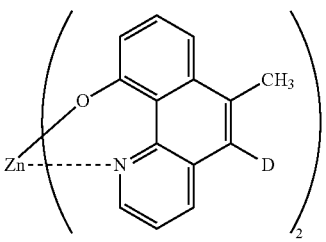

[Chemical Formula 2-10]

The metal complex compound according to another embodiment is represented by the following Chemical Formula 3.

[Chemical Formula 3]

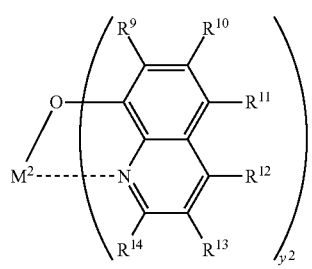

In Chemical Formula 3, $M^2$ is a Group 2 metal ion or Group 3 metal ion, $R^9$ to $R^{14}$ are the same or different, and are hydrogen, deuterium(D), a halogen, a hydroxyl group, a substituted or unsubstituted $C_1$ to $C_{20}$ alkyl group, a substituted or unsubstituted $C_2$ to $C_{20}$ alkenyl group, a substituted or unsubstituted $C_2$ to $C_{20}$ alkynyl group, a substituted or unsubstituted $C_1$ to $C_{20}$ alkoxy group, a substituted or unsubstituted $C_3$ to $C_{30}$ cycloalkyl group, a substituted or unsubstituted $C_3$ to $C_{30}$ cycloalkenyl group, a substituted or unsubstituted $C_3$ to $C_{30}$ cycloalkynyl group, a substituted or unsubstituted $C_2$ to $C_{30}$ heterocycloalkyl group, a substituted or unsubstituted $C_2$ to $C_{30}$ heterocycloalkenyl group, a substituted or unsubstituted $C_2$ to $C_{30}$ heterocycloalkynyl group, a substituted or unsubstituted $C_6$ to $C_{30}$ an aryl group, a substituted or unsubstituted $C_6$ to $C_{30}$ aryloxy group, a substituted or unsubstituted $C_2$ to $C_{30}$ heteroaryl group, an amine group, an ester group, a carboxyl group, a nitro group, or a cyano group, provided that at least one of $R^1$ to $R^8$ is deuterium, and $y^1$ is 2 or 3.

In Chemical Formula 3, $M^2$ may be Be, Zn, Mg, Al, Ga, In or a combination thereof.

The metal complex compound may be represented by one of the following Chemical Formulae 4-1 to 4-10, but are not limited thereto.

[Chemical Formula 4-1]

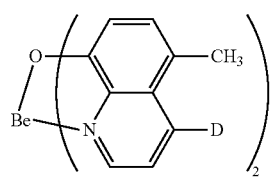

[Chemical Formula 4-2]

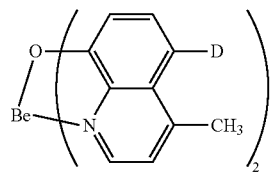

[Chemical Formula 4-3]

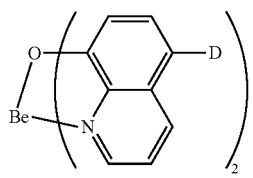

[Chemical Formula 4-4]

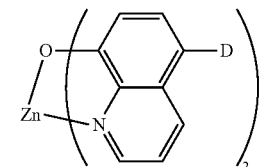

[Chemical Formula 4-5]

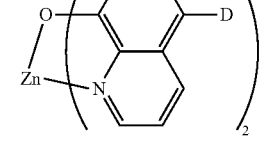

[Chemical Formula 4-6]

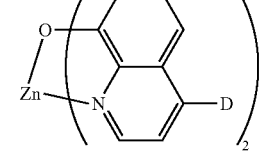

[Chemical Formula 4-7]

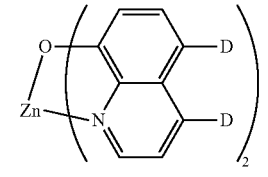

[Chemical Formula 4-8]

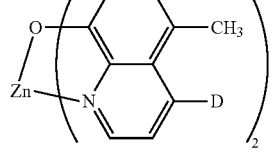

[Chemical Formula 4-9]

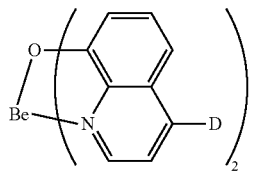

[Chemical Formula 4-10]

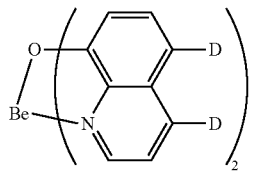

Referring to FIG. 1, an organic light emitting diode device according to one embodiment is described.

FIG. 1 is a schematic cross-sectional view showing an organic light emitting diode device according to one embodiment.

Referring to FIG. 1, the organic light emitting diode device includes a substrate 100, a first electrode 110 disposed on the substrate, an organic layer 120 disposed on the first electrode 110, and a second electrode 130 disposed on the organic layer 120.

The substrate 100 may include a substrate commonly used for an organic light emitting diode device, and in particular, a glass substrate, a plastic substrate, and the like may be used.

The first electrode 110 may be an anode, and may comprise a transparent conductor or an opaque conductor. The transparent conductor may include, for example, ITO (indium tin oxide), IZO (indium zinc oxide), TO (tin oxide), ZnO (zinc oxide), or a combination thereof. The opaque conductor may include silver (Ag), magnesium (Mg), aluminum (Al), platinum (Pt), palladium (Pd), gold (Au), nickel (Ni), neodymium (Nd), iridium (Ir), chromium (Cr), or a combination thereof. When the first electrode 110 is made of a transparent conductor, it may be a bottom emission type emitting light from the bottom.

The organic layer 120 may include at least one layer among a hole injection layer 121, a hole transport layer 123, an emission layer 125, an electron transport layer 127, and an electron injection layer 129 that are sequentially positioned on the first electrode.

The organic layer 120 may include a metal complex compound used for forming at least one layer among the hole injection layer 121, the hole transport layer 123, the emission layer 125, the electron transport layer 127, and the electron injection layer 129. In particular, the metal complex compound may be used to form the emission layer 125 or the electron transport layer 127.

The second electrode 130 may be a cathode and may comprise a transparent conductor or an opaque conductor. The transparent conductor may include ITO (indium tin oxide), IZO (indium zinc oxide), TO (tin oxide), ZnO (zinc oxide), or a combination thereof The opaque conductor may include silver (Ag), magnesium (Mg), aluminum (Al), platinum (Pt), palladium (Pd), gold (Au), nickel (Ni), neodymium (Nd), iridium (Ir), chromium (Cr), or a combination thereof When the second electrode 130 is made of a transparent conductor, it may be a top emission type emitting light from the organic layer 120 to the top.

The organic layer may comprise the metal complex compound, and may increase luminous efficiency of an organic light emitting diode device and decrease its driving voltage.

The following examples illustrate this disclosure in more detail. These examples, however, are not in any sense to be interpreted as limiting the scope of this disclosure.

Preparation Of Metal Complex Compound

Example 1-1

2.0 g (10.3 mmol) of 6-deuterio-10-hydroxybenzo[h]quinoline was put into a reaction vessel, and then 60 ml of a methanol and ethanol mixed solvent (1:1 volume ratio) was put thereto. Dissolution was performed while heating to provide a first solution. 0.91 g (5.15 mmol) of $BeSO_4 \cdot 4H_2O$ was dissolved in 100 ml of pure water to provide a second solution. The first solution was added to the second solution while agitating, pH of the resultant solution was adjusted to be from neutral to weak alkaline, resulting in depositing bluish green precipitate having strong fluorescence. The precipitate was filtered, and dried by heating at 80° C. for 2 hours. The dried precipitate was purified using a sublimation purifying apparatus (H. J. Wagner, R. O. Loutfy and C. K. Hsiao, J. Mater. Sci., 17, 2781 1982), to prepare bis(6-deuterio-10-hydroxybenzo[h]quinolinato)beryllium.

Example 1-2

1.46 g (10.0mmol) of 5-deuterio-8-hydroxyquinoline was put into a reaction vessel, and then 60 ml of a methanol and ethanol mixed solvent (1:1 volume ratio) was put thereto. Dissolution was performed while heating to provide a first solution. 0.89 g (5.0 mmol) of $BeSO_4 \cdot 4H_2O$ was dissolved in 100 ml of pure water to provide a second solution. The first solution was added to the second solution while agitating, pH of the resultant solution was adjusted to be from neutral to weak alkaline, resulting in depositing a green precipitate having strong fluorescence. The precipitate was filtered, and dried by heating at 80° C. for 2 hours. The dried precipitate was purified using a sublimation purifying apparatus to prepare bis(5-deuterio-8-hydroxyquinolinato)beryllium.

Example 1-3

2.10 g (10.0 mmol) of 5-methyl-6-deuterio-10-hydroxybenzo[h]quinoline was put into a reaction vessel, and then 60 ml of a methanol and ethanol mixed solvent (1:1 volume ratio) was put thereto. Dissolution was performed while heating to provide a first solution. 0.89 g (5.0 mmol) of $BeSO_4 \cdot 4H_2O$ was dissolved in 100 ml of pure water to provide a second solution. The first solution was added to the second solution while agitating, pH of the resultant solution was adjusted to be from neutral to weak alkaline, resulting in depositing a green precipitate having strong fluorescence. The precipitate was filtered, and dried by heating at 80° C. for 2 hours. The dried precipitate was purified using a sublimation purifying apparatus to prepare bis(5-methyl-6-deuterio-10-hydroxybenzo[h]quinolinato)beryllium.

Comparative Example 1-1

1.95 g (10.0 mmol) of 10-hydroxybenzo[h]quinoline was put into a reaction vessel, and then 60 ml of a methanol and ethanol mixed solvent (1:1 volume ratio) was put thereto. Dissolution was performed while heating to provide a first solution. $BeSO_4 \cdot 4H_2O$ 0.89 g (5.0 mmol) was dissolved in 100 ml of pure water to provide a second solution. The first solution was added to the second solution while agitating, pH of the resultant solution was adjusted to be from neutral to weak alkaline, resulting in depositing a green precipitate having strong fluorescence. The precipitate was filtered, and dried by heating at 80° C. for 2 hours. The dried precipitate was purified using a sublimation purifying apparatus to prepare bis(10-hydroxybenzo[h]quinolinato)beryllium.

Comparative Example 1-2

1.45 g (10.0 mmol) of 8-hydroxyquinoline was put into a reaction vessel, and then 60 ml of a methanol and ethanol mixed solvent (1:1 volume ratio) was put thereto. Dissolution was performed while heating to provide a first solution. 0.89 g (5.0 mmol) of $BeSO_4 \cdot 4H_2O$ was dissolved in 100 ml of pure water to provide a second solution. The first solution was added to the second solution while agitating, pH of the resultant solution was adjusted to be from neutral to weak alkaline, resulting in depositing a green precipitate having strong fluorescence. The precipitate was filtered, and dried by heating at 80° C. for 2 hours. The dried precipitate was purified using a sublimation purifying apparatus to prepare bis(8-hydroxyquinolinato)beryllium.

Fabrication of an Organic Light Emitting Diode Device

Example 2-1

A lower electrode was prepared by laminating Ag/ITO on a glass substrate and patterning it, and then disposing a hole injection layer to be 70 nm thick on the lower electrode by depositing a compound represented by the following Chemical Formula 5-1, an interlayer to be 5 nm thick thereon by depositing another compound represented by following Chemical Formula 5-2, and a hole transport layer to be 155 nm thick thereon by depositing a compound represented by the following Chemical Formula 5-3. Next, a green phosphorescent red emission layer was disposed to be 40 nm thick by depositing a compound represented by the following Chemical Formula 5-4 as a dopant and bis(6-deuterio-10-hydroxybenzo[h]quinolinato)beryllium prepared in Example 1-1 as a host. Then, an electron transport layer was disposed to be 30 nm thick thereon by depositing a compound represented by the following Chemical Formula 5-5, and an electron injection layer was disposed to be 0.5 nm thick thereon by depositing a compound represented by the following Chemical Formula 5-6. Next, an upper electrode was disposed to be 200 nm thick thereon by depositing MgAg, fabricating an organic light emitting diode device. Herein, the phosphorescent red emission layer included the dopant in an amount of 10 wt % based on the total amount of the emission layer. The electron injection layer was included in an amount of 50 wt % based on the total amount of the electron transport layer and the electron injection layer.

Example 2-2

An organic light emitting diode device was fabricated according to the same method as Example 2-1, except for using the bis(5-deuterio-8-hydroxyquinolinato)beryllium prepared according to Example 1-2 as a host.

Example 2-3

An organic light emitting diode device was fabricated according to the same method as Example 2-1, except for using the bis(5-methyl-6-deuterio-10-hydroxybenzo[h]quinolinato)beryllium prepared according to Example 1-3 as a host.

Comparative Example 2-1

An organic light emitting diode device was fabricated according to the same method as Example 2-1, except for using the bis(10-hydroxybenzo[h]quinolinato)beryllium prepared according to Comparative Example 1-1 as a host.

Comparative Example 2-2

An organic light emitting diode device was fabricated according to the same method as Example 2-1, except for using the bis(8-hydroxyquinolinato)beryllium prepared according to Comparative Example 1-2 as a host.

Evaluation 1

The organic light emitting diode devices according to Examples 2-1 to 2-3 and Comparative Examples 2-1 and 2-2 were evaluated regarding luminous efficiency and color characteristic. The results are provided in the following Table 1.

TABLE 1

| | Voltage (V) | Efficiency (cd/A) | Color coordinates (CIE) x | Color coordinates (CIE) y |
|---|---|---|---|---|
| Example 2-1 | 4.2 | 31 | 0.660 | 0.340 |
| Example 2-2 | 5.1 | 27 | 0.661 | 0.340 |
| Example 2-3 | 4.2 | 30 | 0.661 | 0.339 |
| Comparative Example 2-1 | 4.3 | 26 | 0.661 | 0.338 |
| Comparative Example 2-2 | 5.3 | 24 | 0.660 | 0.339 |

Referring to Table 1, the organic light emitting diode devices according to Examples 2-1 to 2-3 had higher efficiency and similar color coordinates to those according to Comparative Examples 2-1 and 2-2.

While this disclosure has been described in connection with what is presently considered to be practical example embodiments, it is to be understood that the embodiments are not limited to the disclosed embodiments, but, on the contrary, is intended to cover various modifications and equivalent arrangements included within the spirit and scope of the appended claims.

What is claimed is:

1. A metal complex compound represented by the following Chemical Formula 1:

[Chemical Formula 1]

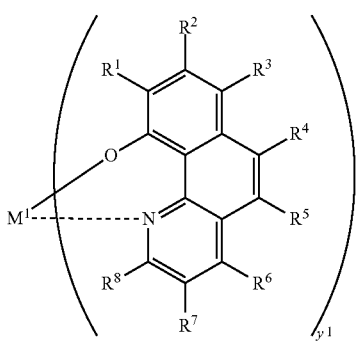

wherein, in Chemical Formula 1,
$M^1$ is a Zn, Al, Ga, In, a Group 2 metal ion or Group 3 metal ion,
$R^1$ to $R^8$ are the same or different, and are independently selected from the group consisting of hydrogen, deuterium, a halogen, a hydroxyl group, a substituted or unsubstituted $C_1$ to $C_{20}$ alkyl group, a substituted or unsubstituted $C_2$ to $C_{20}$ alkenyl group, a substituted or unsubstituted $C_2$ to $C_{20}$ alkynyl group, a substituted or unsubstituted $C_1$ to $C_{20}$ alkoxy group, a substituted or unsubstituted $C_3$ to $C_{30}$ cycloalkyl group, a substituted or unsubstituted $C_3$ to $C_{30}$ cycloalkenyl group, a substituted or unsubstituted $C_3$ to $C_{30}$ cycloalkynyl group, a substituted or unsubstituted $C_2$ to $C_{30}$ heterocycloalkyl group, a substituted or unsubstituted $C_2$ to $C_{30}$ heterocycloalkenyl group, a substituted or unsubstituted $C_2$ to $C_{30}$ heterocycloalkynyl group, a substituted or unsubstituted $C_6$ to $C_{30}$ an aryl group, a substituted or unsubstituted $C_6$ to $C_{30}$ aryloxy group, a substituted or unsubstituted $C_2$ to $C_{30}$ heteroaryl group, an amine group, an ester group, a carboxyl group, a nitro group, and a cyano group, wherein at least one of $R^4$ to $R^5$ is deuterium and at least one of $R^1$ to $R^8$ is hydrogen,
wherein only one of $R^1$ to $R^8$ is deuterium,
wherein at least one of $R^4$ and $R^5$ is methyl, and
wherein $y^1$ is 2 or 3.

2. The metal complex compound of claim 1, wherein in Chemical Formula 1, $M^1$ is Be, Zn, Mg, Al, Ga, In, or a combination thereof.

3. The metal complex compound of claim 1, wherein the metal complex compound is represented by one of the following Chemical Formulae 2-4, 2-5, 2-9, and 2-10:

[Chemical Formula 2-4]

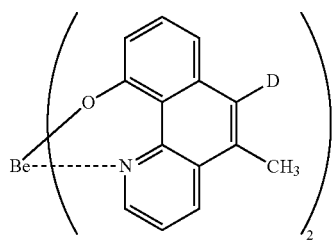

[Chemical Formula 2-5]

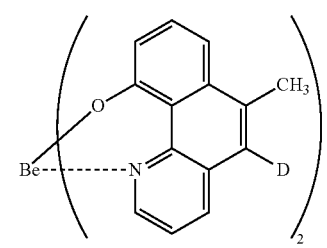

[Chemical Formula 2-9]

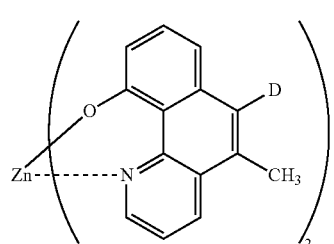

[Chemical Formula 2-10]

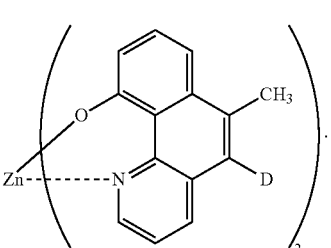

4. An organic light emitting device comprising
a first electrode,
a second electrode facing the first electrode, and
an organic layer interposed between the first electrode and the second electrode,
wherein the organic layer includes a metal complex compound represented by the following Chemical Formula 1:

[Chemical Formula 1]

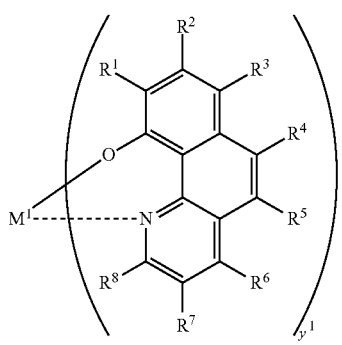

wherein, in Chemical Formula 1, $M^1$ is a Zn, Al, Ga, In, a Group 2 metal ion or Group 3 metal ion, $R^1$ to $R^8$ are the same or different, and are independently selected from the group consisting of hydrogen, deuterium, a halogen, a hydroxyl group, a substituted or unsubstituted $C_1$ to $C_{20}$ alkyl group, a substituted or unsubstituted $C_2$ to $C_{20}$ alkenyl group, a substituted or unsubstituted $C_2$ to $C_{20}$ alkynyl group, a substituted or unsubstituted $C_1$ to $C_{20}$ alkoxy group, a substituted or unsubstituted $C_3$ to $C_{30}$ cycloalkyl group, a substituted or unsubstituted $C_3$ to $C_{30}$ cycloalkenyl group, a substituted or unsubstituted $C_3$ to $C_{30}$ cycloalkynyl group, a substituted or unsubstituted $C_2$ to $C_{30}$ heterocycloalkyl group, a substituted or unsubstituted $C_2$ to $C_{30}$ heterocycloalkenyl group, a substituted or unsubstituted $C_2$ to $C_{30}$ heterocycloalkynyl group, a substituted or unsubstituted $C_6$ to $C_{30}$ an aryl group, a substituted or unsubstituted $C_6$ to $C_{30}$ aryloxy group, a substituted or unsubstituted $C_2$ to $C_{30}$ heteroaryl group, an amine group, an ester group, a carboxyl group, a nitro group, and a cyano group, wherein at least one of $R^4$ to $R^5$ is deuterium and at least one of $R^1$ to $R^8$ is hydrogen, wherein only one of the $R^1$ to $R^8$ is deuterium, wherein at least one of $R^4$ and $R^5$ is methyl, and wherein $y^1$ is 2 or 3.

5. The organic light emitting diode device of claim 4, wherein the organic layer comprises at least one among a hole injection layer (HIL), a hole transport layer (HTL), an emission layer, an electron transport layer (ETL), and an electron injection layer (EIL) that are sequentially positioned on the first electrode.

6. The organic light emitting diode device of claim 5, wherein the metal complex compound is included in the emission layer.

7. The organic light emitting diode device of claim 5, wherein the metal complex compound is included in the electron transport layer (ETL).

8. The organic light emitting diode device of claim 4, wherein in Chemical Formula 1, $M^1$ is Be, Zn, Mg, Al, Ga, In, or a combination thereof.

9. The organic light emitting diode device of claim 4, wherein the metal complex compound is represented by one of the following Chemical 2-4, 2-5, 2-9, and 2-10:

[Chemical Formula 2-4]

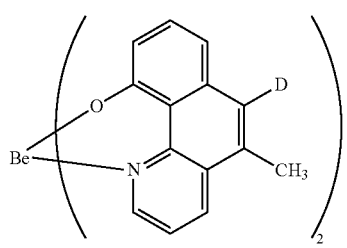

[Chemical Formula 2-5]

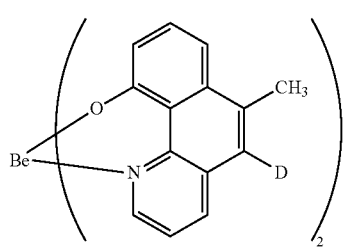

[Chemical Formula 2-9]

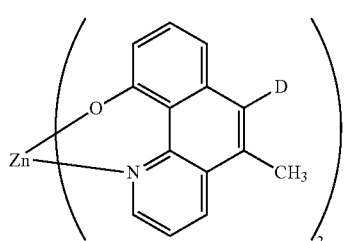

[Chemical Formula 2-10]

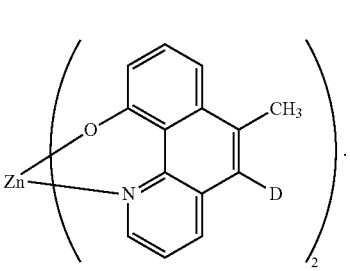

* * * * *